US005922928A

United States Patent [19]
Chiang et al.

[11] Patent Number: 5,922,928
[45] Date of Patent: Jul. 13, 1999

[54] GENETIC TRANSFORMATION AND REGENERATION OF PLANTS

[75] Inventors: Vincent Lee C. Chiang; Chung Jui Tsai, both of Hancock; Gopi K. Podila, Houghton, all of Mich.

[73] Assignee: Board of Control of Michigan Technological University, Houghton, Mich.

[21] Appl. No.: 08/757,576

[22] Filed: Nov. 27, 1996

Related U.S. Application Data

[60] Provisional application No. 60/007,727, Nov. 30, 1995.
[51] Int. Cl.$^6$ .......................... C12N 15/00; C12N 15/29; C12N 15/82; A01H 5/00
[52] U.S. Cl. ......................... 800/278; 800/284; 800/290; 800/294; 800/298; 435/440; 435/468; 435/320.1; 536/236; 536/24.1
[58] Field of Search ........................... 800/205; 536/23.6, 536/24.1; 435/172.3, 320.1

[56] References Cited

U.S. PATENT DOCUMENTS

| 4,795,855 | 1/1989 | Fillatti et al. ................................. 800/1 |
| 5,451,514 | 9/1995 | Boudet et al. ........................ 435/172.3 |

FOREIGN PATENT DOCUMENTS

| 2005597 | 6/1990 | Canada ........................... C12N 15/00 |
| WO 93/05160 | 3/1993 | WIPO ............................. C12N 15/54 |

OTHER PUBLICATIONS

Vignols et al. The Plant Cell. vol. 7, 407–416, Apr. 1995.
Bugos et al. Plant Molecular Biology 17: 1203–1215, 1991.
Robert C. Bugos, et al., "Characterization of Bispecific Caffeic Acid/5–Hydroxyferulic Acid O–Methyltransferase from Aspen", *Phytochemistry*, vol. 31, No. 5, pp. 1495–1498, 1992.
Robert C. Bugos, et al., "Isolation of O–Methyltransferase Associated with Lignin Biosynthesis in Aspen", International Symposium on Wood and Pulping Chemistry, NC State University, Raleigh, NC May 22–25, 1989.
Robert C. Bugos, et al., "cDNA cloning, sequence analysis and seasonal expression of lignin–bispecific caffeic acid/5–hydroxyferulic acid O–methyltransferase of aspen", Plant Molecular Biology 17: 1203–1215, 1991.
Chung–Jui Tsai, et al., "Agrobacterium–mediated transformation of quaking aspen (*Populus tremuloides*) and regeneration of transgenic plants", Plant Cell Reports 14:94–97, 1994.

Csaba Koncz, et al., "The promoter of $T_L$–DNA gene 5 controls the tissue–specific expression of chimaeric genes carried by a novel type of Agrobacterium binary vector", Mol Gen Genet 204: 383–396, 1986.

V.L. Chiang, et al., "Regulation of Lignin Biosynthesis in Transgenic Quaking Aspen (*Populus tremuloides*)", Biological Sciences Symposium, Minneapolis, MN Oct. 3–6, 1994.

Michael H. Walter, et al., "Cinnamyl–alcohol dehydrogenase, a molecular marker specific for lignin synthesis: cDNA cloning and mRNA induction by fungal elicitor", Proc. Natl. Acad. Sci. USA, vol. 85, pp. 5546–5550, Aug. 1988.

Csaba Koncz, et al., "The promoter of $T_L$–DNA gene 5 controls the tissue–specific expression of chimaeric genes carried by a novel type of *Agrobacterium* binary vector", Mol Gen Genet 204: 383–396, 1986.

Jan Van Doorsselaere, et al., "A novel lignin in poplar trees with a reduced caffeic acid/5–hydroxyferulic acid O–methyltransferase activity", The Plant Journal 8(6), 855–864, 1995.

Dennis L. Bucholtz, et al., "Lignin Biochemistry of Normal and Brown Midrib Mutant Sorghum", *J. Agric. Food Chem*, vol. 28, No. 6, pp. 1239–1241, 1980.

Christian Pillonel, et al., "Involvement of cinnamyl–alcohol dehydrogenase in the control of lignin formation in Sorghum bicolor L. Moench", *Planta*, 185: 538–544, 1991.

Takayoshi Higuchi, "Biosynthesis of lignin", *Biosynthesis and Biodegradation of Wood Components*, Orlando FL: Academic Press, pp. 141–160, 1985.

Takashi Hibino, et al., "Increase of Cinnamaldehyde Groups in Lignin of Transgenic Tobacco Plants Carrying an Antisense Gene for Cinnamyl Alcohol Dehydrogenase", *Biosci. Biotech. Biochem*, 59, 929–931, 1995.

Claude Grand, "Ferulic acid 5–hydroxylase: a new cytochrome P–450–dependent enzyme from higher plant microsomes involved in lignin synthesis", *Federation of European Biochemical Societies*, vol. 169, No. 1, Apr. 1984.

*Primary Examiner*—Douglas W. Robinson
*Assistant Examiner*—Thomas Haas
*Attorney, Agent, or Firm*—Michael Best & Friedrich LLP

[57] ABSTRACT

An Agrobacterium-mediated transformation and regeneration method for plants including a transformation method to produce transgenic plants with an altered lignin composition.

33 Claims, 2 Drawing Sheets

5,922,928

GENETIC TRANSFORMATION AND REGENERATION OF PLANTS

RELATED APPLICATION

This application claims the benefit of prior filed, copending provisional application Ser. No. 60/007,727 filed Nov. 30, 1995 entitled "GENETIC MODIFICATION OF ANGIOSPERM PULPWOOD SPECIES".

FIELD OF THE INVENTION

The invention relates to a method to genetically modify and regenerate Populus species, and to a transformation and regeneration method for producing transgenic angiosperms with altered lignin composition.

BACKGROUND OF THE INVENTION

Genetic engineering of forest tree species to conform to desired traits has shifted the emphasis in forest tree improvement away from traditional breeding programs. Although research on genetic engineering of forest trees has been vigorous, the progress has been slow due either to a lack of an efficient gene transfer mechanism or lack of an in vitro culture system for plant regeneration.

Of Populus species, quaking aspen is one of the most commonly used species for wood pulp production in North America due to its good fiber properties, fast growth, and world-wide distribution. In addition to these characteristics desired for a pulpwood species, it is economically beneficial to genetically engineer new traits into Populus species such as quaking aspen such as altered lignin composition.

The only known Agrobacterium-mediated transformation and regeneration of quaking aspen was reported in 1986 using hypocotyl and leaf segments of in vitro plants derived from seedlings. However, this and other techniques developed for Populus species are not capable of regenerating whole plant from plant tissue derived from field-grown and greenhouse-grown plants or require tissue from in vitro plants. It is known that whole plant regeneration from greenhouse-grown plant materials is more difficult than that from in vitro plant materials or embryonic materials including mature and immature embryo, cotyledon, hypocotyl, and seedling.

A transformation and regeneration method for greenhouse and field-grown plants is needed for Populus species such as quaking aspen. The continual availability of field-grown as well as greenhouse-grown plants through vegetative propagation and the ease of maintaining these plants are the obvious advantages of using greenhouse and field-grown plants over the use of in vitro plants derived from seedlings. However, the difficulty of shoot regeneration from greenhouse and field-grown plants has been one of the main reasons that in vitro plants from seedlings have been the preferred explant materials.

With respect to lignin, angiosperm lignin also called guaiacyl-syringyl lignin is formed from the polymerization of two main precursors: coniferyl alcohol and sinapyl alcohol. The ratio of syringyl to guaiacyl units is directly related to the efficiency of kraft delignification, with higher syringyl quantities improving the pulping efficiency. There is a need for altering the lignin composition in that it is economically beneficial to genetically alter lignin composition to increase the ratio of syringyl to guaiacyl units for some applications and reduce the ratio for other applications. For example, pulping by the paper industry would be made more efficient with plants having a higher ratio of syringyl to guaiacyl units and novel wood would be available having a lower ratio of syringyl to guaiacyl units.

SUMMARY OF THE INVENTION

The invention relates to a method for genetic transformation and regeneration of plants. For example, the method of the present invention can be used for generating transgenic Populus species with altered lignin composition. Regulation of the expression of a lignin-pathway specific gene, for example, O-methyltransferase, through transformation can genetically manipulate the composition of lignin. The invention also provides a method for altering the composition of lignin in plants.

The method of the present invention allows an efficient whole plant regeneration from cuttings of greenhouse-grown as well as field-grown mature trees. This method circumvents the difficulty of whole plant regeneration from greenhouse-grown and field-grown trees. The method includes an Agrobacterium-mediated transformation of plants such as greenhouse or field-grown Populus species and the regeneration of whole plants from the transformed callus through the introduction of thidiazuron as a plant growth regulator.

It is an object of the present invention to provide an improved transformation and regeneration method for Populus species.

It is another object of the present invention to provide a method to transform greenhouse and field-grown plants and then to regenerate the transgenic plants.

It is another object of the present invention to produce a regeneration method that circumvents the difficulty of whole plant regeneration from greenhouse and field-grown plants.

It is another object of the present invention to genetically altered the composition of lignin of angiosperms through the transformation and regeneration of the transgenic plants.

It is another object of the present invention to genetically alter the lignin composition of angiosperms through transforation of the species with the lignin pathway gene O-methyltransferase.

It is another object of the present invention to alter the lignin composition of angiosperms such that the transgenic plants are easier to pulp.

It is another object of the present invention to alter the lignin composition of angiosperms such that the ratio of syringyl to guaiacyl units is increased.

It is another object of the present invention to alter the lignin composition of angiosperms such that the ratio of syringyl to guaiacyl units is decreased.

Other features and advantages of the invention will become apparent to those of ordinary skill in the art upon review of the following detailed description.

Figure 1:
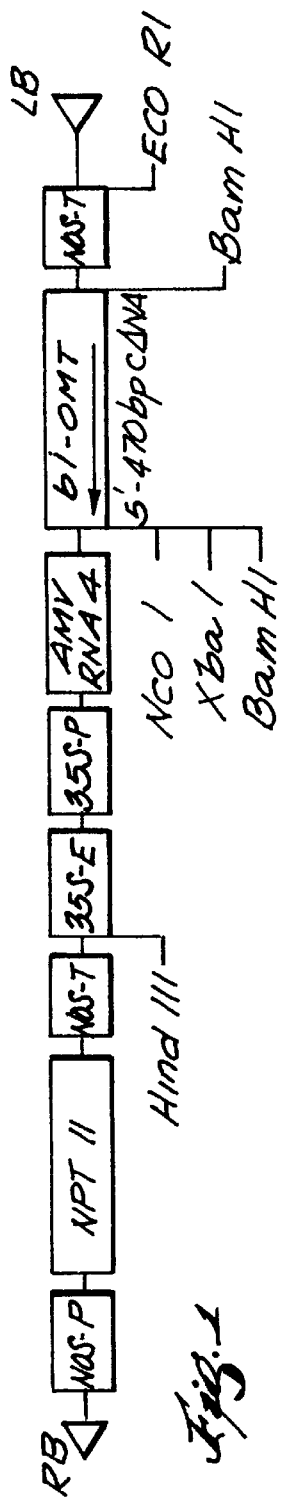
FIG. 1 is a diagram of gene construct pAOMT2.

Before one embodiment of the invention is explained in detail, it is to be understood that the invention is not limited in its application to the details set forth in the following description. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

The invention provides for a transformation and regeneration method for plants of the Populus species. The method will be described below using the Populus species quaking aspen (*Populus tremuloides*). However, it should be noted that the transformation and regeneration method is applicable to other Populus species such as, for example, hybrid poplar, cottonwood and hybrid cottonwood.

All of the culture media used in this method include the basal medium of woody plant medium (WPM) as described in Lloyd and McCown, Proc. Int. Plant Prop. Soc. 30:421–437 (1980) supplemented with 2% sucrose and 650 mg/L calcium gluconate and 500 mg/L MES are added as pH buffers as described in De Block, Plant Physiol. 93:1110–1116 (1990). The callus induction medium is the basal medium with the addition of 0.5 mg/L 6-benzyladenine (BA) and 1 mg/L 2,4-dichlorophenoxyacetic acid (2,4-D). The shoot regeneration medium is the basal medium containing 0.5 mg/L thidiazuron (TDZ) as a plant growth regulator. The elongation medium is hormone free basal medium. The rooting medium is hormone free basal medium. For selecting transformed tissue, the antibiotic kanamycin is used in the callus induction medium, the shoot regeneration medium, the elongation medium and the rooting medium as will be described below.

All culture media are adjusted to pH 5.5 prior to the addition of 0.75% Difco Bacto Agar and then autoclaved at 121° C. and 15 psi for 20 minutes. Antibiotics are filtered sterilized and added after autoclaving. All cultures are maintained at 23±1° C. in a growth chamber with 16 hour photoperiods (160 $\mu$E x $m^{-2}$ x $S^{-1}$) except for callus induction which is maintained in the dark.

A binary vector containing the gene to be transformed is mobilized into a strain of Agrobacterium species, such as tumefaciens strain C58. Preferably, the vectors are mobilized into Agrobacterium using the freeze-thaw method of Holstein et al., Mol. Gen. Genet. 163:181–187 (1978). The Agrobacterium is streaked on a LB plate containing appropriate antibiotics and incubated preferably at 28° C. for two days. One isolated colony of Agrobacterium is chosen and inoculated with 5 mL of LB (pH 7.0) and antibiotics and grown overnight at 28° C. in a shaker. The Agrobacterium is subcultured by diluting 1:100 into 20 mL of LB (pH 5.4) containing suitable antibiotics and 20 $\mu$M acetosyringone (AS) and grown overnight at 28° C. with shaking.

Young leaves from cuttings of Populus species are excised and surface sterilized in 20% commercial bleach with a few drops of Tween-20 for 10 minutes followed by rinsing three times with sterile double-distilled water. The sterilized leaves are cut into 7 mm squares along the midrib with preferably five wounds on the rib.

The leaf pieces are dipped into the overnight-grown Agrobacterium solution and inoculated for at least five minutes. After infection, the explants are blotted dry on sterile filter papers to remove excess Agrobacterium. The explants are placed upside down on callus induction medium and cocultivated for two days in the dark.

After cocultivation, the explants are washed several times with sterile distilled water to remove most of the bacteria. Damaged leaf discs from previous handling can be eliminated at this point. The explants are then washed with sterile distilled water containing 1 mg/mL claforan and 1 mg/mL ticarcillin for one to two hours with shaking to kill Agrobacterium. The explants are blotted dry with sterile filter papers and transferred onto callus induction medium containing 300 mg/L claforan and 50 mg/L kanamycin for selection of transformed cells.

The kanamycin-resistant explants are first subcultured after one week and then transferred to fresh callus induction media every other week thereafter. Agrobacterium come back mostly within the first month. Leaf discs with Agrobacterium attached should be sacrificed. If the recovery of Agrobacterium extends to a high degree, the above described washing step is repeated. A prolonged washing period such as overnight or up to one day in antibiotic solution may also help.

Callus formation occurs at the wound sites of midribs of the explants after about four weeks. Formed callus are separated from the explant and subcultured periodically for further proliferation.

When the callus clumps reach approximately 3 mm in diameter, the callus clumps are excised and transferred to shoot regeneration medium containing 50 mg/L kanamycin and 300 mg/L claforan. Shoot regeneration starts appearing about four to six weeks after callus is transferred to the shoot regeneration medium.

As soon as the shoots are regenerated, the entire callus clump is transferred to the elongation medium containing 50 mg/L kanamycin and, whenever necessary, 300 mg/L claforan to promote elongation. Claforan can be omitted from the culture media if the Agrobacterium are not present. Green and healthy shoots elongated to approximately 2–3 cm in length are excised and planted separately in the rooting medium containing 100 mg/L kanamycin. The efficient uptake of kanamycin by shoots during their rooting stage provides the most effective selection for positive transformants. During rooting stage, shoots if any that apparently escaped from previous selections develop reddish leaves with black spots and necrosis in both shoot and leaves within two weeks and eventually die. Regenerated plants that survived the selection at rooting stage form roots within two weeks in fresh rooting medium.

Transgenic plants are then transplanted into soil medium of vermiculite, peatmoss and perlite at a 1:1:1 ratio and grown in the greenhouse.

Factors influencing the transfer efficiency were examined in order to optimize the transformation and regeneration method. The effects of a preculture period and the effects of the acetosyringone (AS) on transformation efficiency were investigated with the following results.

A preculture period consisted of culturing the sterilized explants on callus induction medium for a period of days to screen for healthy leaf disks prior to inoculation with the Agrobacterium. It was determined that preculturing explants significantly lowered the transformation efficiency. The effect was more pronounced as the preculturing period increased. With respect to the addition of the phenolic AS, AS at the level of 20 $\mu$M enhanced the transformation efficiency.

The preculturing and AS results suggest that phenolic compounds produced by freshly wounded tissues have a stronger effect than artificially added phenolics such as AS in triggering the activation of bacterial vir genes. This was supported by the data that frequencies of transformed callus from the preculture treatments with the addition of AS were all lower than that of the treatment without preculture and AS. A possible explanation is that the plant phenolics extruded into the media during preculture were excluded from the explants when they were inoculated with Agrobacterium and co-cultivated onto fresh media.

In the presence of 20 $\mu$M AS, for example, 30% of inoculated explants of quaking aspen could produce callus on selection medium without preculture treatment. When the transformed calli were proceeded to further developmental stages, approximately 40% of the transformed calli were able to form shoots and rooted plantlets in kanamycin-containing medium. An overall transformation frequency of 12% was obtained from the optimized condition which required the addition of AS without preculturing explants.

Shoot regeneration cannot be achieved from callus derived from greenhouse aspen leaves when the common growth regulators 6-benzyladenine or 1-naphthylacetic acid are used. However, shoot regeneration is successful when these common regulators are replaced by thidiazuron (TDZ) in the concentration range of 0.05 to 1 mg/L. At high concentrations of TDZ, however, swelling or vitrification of shoots and, in some cases, inhibition of shoot elongation occurs. To avoid these adverse effects, shoot regeneration is conducted on medium containing 0.5 mg/L TDZ and shoots are transferred onto elongation medium immediately after their formation. In this way, satisfactory shoot regeneration and elongation is achieved from leaves of greenhouse-grown and cuttings of field-grown mature Populus species.

The above described transformation and regeneration method is a reliable and efficient method for transferring genes to Populus species. Genes can be transferred in a sense or antisense orientation into leaf tissue and regenerated so that the new plants express the introduced genes.

Of particular interest to the paper industry, is the transfer of lignin pathway genes to Populus species to alter the quantity and quality of lignin. For example, several lignin biosynthesis pathway-specific genes have been cloned from quaking aspen. These include genes encoding caffeic acid/5-hydroxyferulic acid O-methyltransferase (OMT), cinnamic acid 4-hydroxylase (C4H), 4-hydroxycinnamic acid CoA ligase (4CL) and caffeoyl-CoA-3-O-methyltransferase (CCoAOMT) enzymes. The above described transformation and regeneration method is a reliable and efficient method for transferring lignin pathway genes into Populus plant tissue in sense or antisense orientation from which whole plants that express these introduced lignin biosynthesis pathway-specific genes are produced.

The following examples are intended to be illustrative and not intended to be limiting in any way.

EXAMPLE I

The transformation and regeneration method described above was utilized for the Agrobacterium-mediated transformation of chimeric neomycin phosphotransferase II (NPTII) and β-glucuronidase (GUS) genes to greenhouse-grown quaking aspen.

The binary vector BinSynGus containing double 35S promotor/alfalfa mosaic virus (AMV) RNA4-untranslated region/GUS/NOS gene fusion with the NOS/NPT II/NOS gene cassette was mobilized into *Agrobacterium tumefaciens* strain C58 by freeze-thaw method of Holstein et al., Mol. Gen Genet. 163:181–187 (1978).

Transformed and regenerated plants were subjected to polymerase chain reaction (PCR), Southern analyses and GUS expression assay to verify the integration of GUS and NPT II genes in nuclear genome of these plants.

To confirm transformation using PCR, PCR analysis based upon the modified method of Edwards et al., Nucleic Acids Res. 19(6):1349–1352 (1991), was used. NPT II and GUS primers (Blake et al., Crop Sci. 31:1686–1688 (1991)) bordering a 780 bp fragment of NPT II and 1097 bp fragment of GUS genes, are used for PCR. The template DNA for PCR was extracted from a single leaf excised from control untransformed and transgenic plants. The leaf was first ground in liquid nitrogen in a microcentrifuge tube and homogenized in 400 μL extraction buffer (200 μM Tris-HCl pH 7.5, 250 μM NaCl, 25 μM EDTA, 0.5% sodium dodecyl sulphate (SDS)) for 30 seconds and followed by phenol/chloroform and chloroform extractions. After precipitation in ethanol, DNA was pelleted and dissolved in 20 μL Tris-CL/EDTA (TE) buffer. PCR reactions (final volume=50 μL) were performed using 5 μL of template DNA. Samples were heated to 95° C. for 4 minutes, followed by 35 cycles of 95° C. for 45 seconds, 55° C. for 30 seconds, and 73° C. for 2.5 minutes with a final extension step of 73° C. for 5 minutes in a thermal cycler (Perkin Elmer/Cetus 480). Amplified DNA fragments were electrophoresed on a 0.8% agarose gel and visualized by straining with ethidium bromide.

PCR analysis reveals that 1097 bp GUS and 785 bp NPT II DNA fragments were amplified from genomic DNA of all putative transgenic plants. However, no GUS and NPT II PCR products were seen for the control non-transformed plants. PCR analysis indicates transformation of GUS and NPT II genes into these putative transgenic plants.

To confirm transformation using Southern analysis, total cellular DNA was isolated from young aspen leaves according to Aitchitt et al., Plant Mol. Biol. Reporter 11(4):317–319 (1993). 10 μg of DNA was digested with 2 units/μg DNA of Eco RI, Hind III, or Eco RI and Hind III at 37° C. overnight and was fractionated on a 0.8% agarose gel and blotted to nylon membrane. The blot was probed with randomly primed $^{32}$P-labelled probe of either NPT II or GUS DNA fragment from BinSynGus vector. Hybridization and washing of the blot were carried out at high stringency and the blot was autoradiographed according to Bugos et al., Plant Mol. Biol. 17:1203–1215 (1991).

The results of the analysis of three putative transgenic plants demonstrated that $^{32}$P-labelled NPT II probe hybridized to various DNA fragments of transgenic plants and non-digested BinSynGus plasmid, but no hybridization was seen for control non-transformed aspen, indicating positive integration of NPT II gene into the genome of transgenic plants. Furthermore, a different pattern of multiple hybridization was observed for the transgenic plants. For instance, NPT II probe hybridizes to three, two and one DNA fragments of genomic DNA restricted with Eco RI for these three transgenic plants, respectively. Similarly, a different pattern of multiple hybridization is also observed for these three transgenic plants of which genomic DNA was digested with Hind III. This hybridization of NPT II probe to multiple DNA fragments indicates a random integration and multiple insertions of NPT II gene in genome of transgenic plants, which is typical for Agrobacterium-mediated gene transformation of plants.

Likewise, Southern analysis with $^{32}$P-labelled GUS DNA on transgenic aspen genomic DNA double digested with Eco RI and Hind III revealed a strongly hybridizing DNA fragment at about 3 kb, an expected size for the GUS gene cassette (double cauliflower mosaic virus (CaMV) 35S promoter/AMV RNA4/GUS/NOS). The above results clearly provide evidence that GUS and NPT II genes were integrated in the genome of transgenic aspen, confirming the validity of this Agrobacterium-mediated gene transformation and regeneration of the transgenic plant systems for quaking aspen.

In addition to PCR and genomic Southern hybridization analyses, in situ GUS activity with 5-bromo-4-chloro-3-indoyl-β-glucuronic acid (X-GLUC) was also conducted for control and transgenic plants to further confirm the expression of GUS gene in these plants. Leaves, roots and stems from regenerated and kanamycin-resistant plants were analyzed for GUS gene expression in situ with X-GLUC according to Jefferson et al., Plant Mol. Biol. 5:387–405 (1987). Plant materials were stained with 1 mM X-GLUC in 100 mM phosphate buffer (pH 7.0) containing 10 mM EDTA (pH 7.0), 0.5 mM potassium ferrocyanide, 0.5 mM potassium ferricyanide, and 0.1% Triton X-100 at 37° C. overnight. After staining, plant tissues were soaked in hot 70% ethanol to clear chlorophyll and were subsequently fixed in formalin-acetic acid/alcohol (FAA) for one day, followed by dehydration in t-butanol-ethanol series and embedded in paraffin. After removal of paraffin, tissue sections of 15 $\mu$m in thickness were photographed with a Nikon Optiphot light microscope.

An intense blue staining was observed from tissues of leaf, stem and root of transgenic plants, but no staining was seen for control non-transformed plants, confirming positive transformation and expression of T-DNA in these transgenic plants.

EXAMPLE II

Using the above transformation and regeneration method, the following gene constructs can be transferred into quaking aspen.

A. The pAOMT2 gene fragment construct of aspen OMT cDNA in an antisense orientation as illustrated in FIG. 1.

Figure 2:
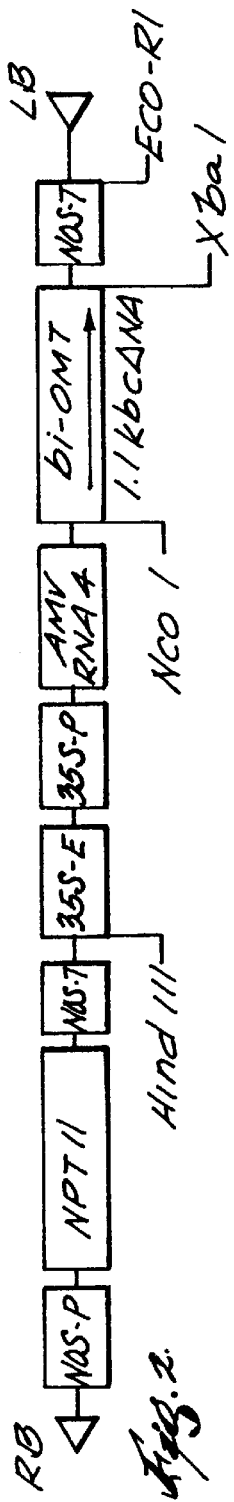
FIG. 2 is a diagram of gene construct pFOMT1.

B. The pFOMT1 gene construct of aspen OMT cDNA in a sense orientation as illustrated in FIG. 2.

Figure 3:
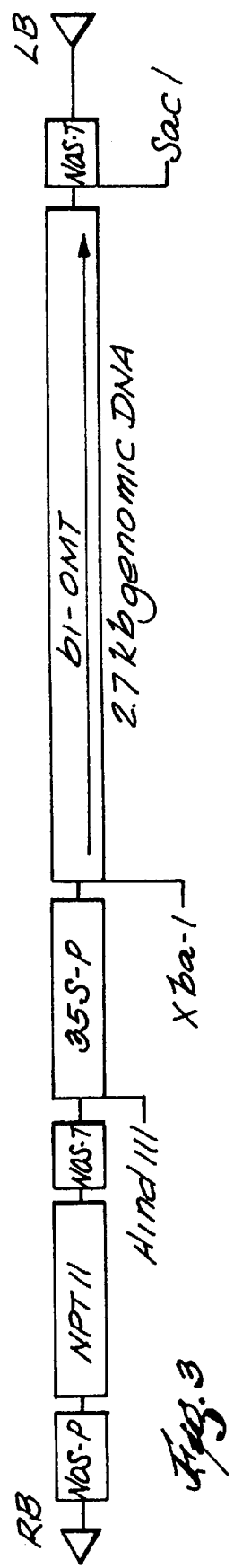
FIG. 3 is a diagram of gene construct pFOMT2.

C. The pFOMT2 gene construct of aspen 2.7 kb genomic OMT DNA in a sense orientation as illustrated in FIG. 3.

Figure 4:
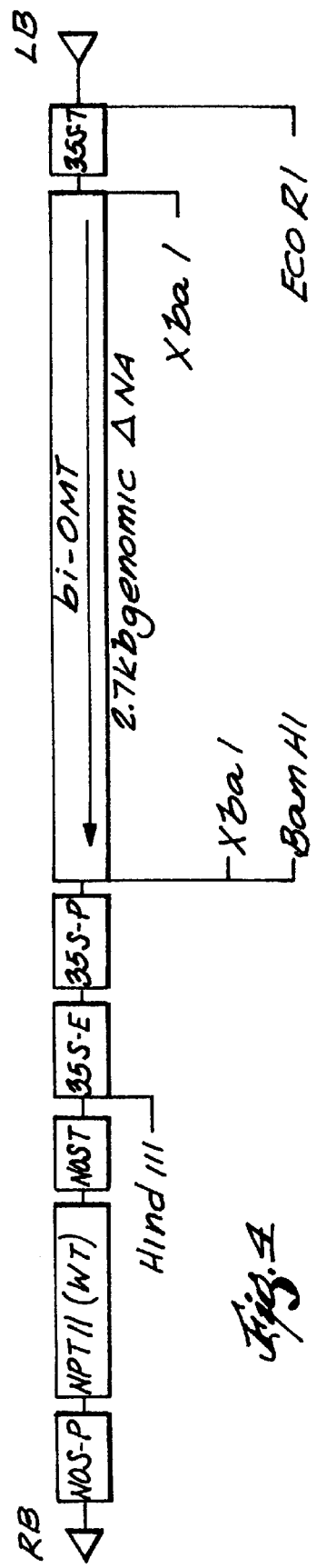
FIG. 4 is a diagram of gene construct pAOMT3.

D. The pAOMT3 gene fragment construct of aspen genomic OMT in an antisense orientation as illustrated in FIG. 4.

E. A gene construct containing eucalyptus OMT cDNA in an antisense orientation. The construct for this gene is similar to the construct pAOMT2 of FIG. 1 in which aspen OMT cDNA was replaced with eucalyptus OMT cDNA.

All of the above OMT genes and cDNA were driven by cauliflower mosaic virus (CaMV) 35S promoter.

Each binary vector was mobilized into *Agrobacterium tumefaciens* strain C58/pMO90 to infect aspen leaf pieces from which whole transgenic plants were produced according to the above described regeneration method.

The vectors and gene constructs of FIGS. 1 through 4 are described in the Ph.D. Dissertation of Chung Jui Tsai titled "Generic Engineering of Quaking Aspen Through Agrobacterium-Mediated Transformation for Modification of Lignin Biosynthesis (1995) available from Michigan Technological University, Houghton, Mich. and incorporated herein by reference. The gene constructs are also available from Michigan Technological University, Institute for Wood Research, Houghton, Mich.

The invention further provides a method for altering the lignin composition of angiosperms. Lignin that is altered to increase the ratio of syringyl to guaiacyl units increases the efficiency of kraft delignification. Angiosperms with higher ratios can be used for producing wood pulp at reduced operating costs in terms of energy and materials. Angiosperms with higher ratios are useful for their novel wood.

The lignin composition is altered through transformation of plants with homologous or heterologous OMT genes in the sense or antisense orientation. Transformation with an OMT gene apparently has no effect on lignin quantity only lignin composition.

The cDNA clone encoding aspen bi-specific OMT and its sequence is described in Bugos et al., Plant Molecular Biology 17:1203–1215 (1991) which is herein incorporated by reference as well as co-pending Ser. No. 08/715,325 filed Sep. 18, 1996 which is also incorporated herein by reference. The clone is also available from Michigan Technological University, Institute for Wood Research, Houghton, Mich.

The following examples are intended to be illustrative and not intended to be limiting in any way.

EXAMPLE III

Using the above described transformation and regeneration method, a homologous antisense O-methyltransferase gene driven by cauliflower mosaic virus (CaMV) 35S promoter was introduced into the Populus species quaking aspen as follows.

A 5' 470 bp coding sequence of aspen bi-OMT gene was blunt and cloned into the Sma I site of pUC 18 for selection of bi-OMT gene fragment with reverse orientation. The Xba I-Sac I fragment of antisense bi-OMT gene was released from pUC 18 and cloned into pFF19 digested with Xba I and Sst I. The Eco RI-Hind III fragment from pFF19 contained a 1.4 kb gene cassette of 35S enhancer/35S promotor/antisense bi-OMT/35 terminator was cloned into a NPT II containing binary vector pRD410 to replace its GUS/NOS fragment released by Eco RI and Hind III digestion to generate the binary vector pAOMT2 as illustrated in FIG. 1. pAOMT2 was mobilized into *Agrobacterium tumefaciens* strain C58 using the freeze-thaw method of Holstein et al., Mol. Gen. Genet. 163:181–187 (1978) and transformed into aspen leaf disks. Kanamycin-resistant aspen transformants were generated through Agrobacterium-mediated transformation with the pAOMT2 antisense gene construct using the transformation and regeneration method described above. The in vitro rooted transformants were first confirmed by PCR using primers bordering a 785 bp fragment of NPT II gene as described above. When confirmed, the transgenic plants were transplanted into soil and grown in the greenhouse.

Transgenic plants were chosen for molecular genetic analysis along with one wild-type aspen obtained from the same regeneration system without transformation and one transgenic aspen with the GUS gene as described above (hereafter "GUS plant") grown in the greenhouse were also used as controls in the assays.

Total cellular DNA was isolated from young leaves of the transgenic aspen as described previously in EXAMPLE I. Ten $\mu$g of DNA were digested with either Hind III, Xba I or Hind III+Xba I and fractionated on a 0.8% agarose gel. The gels were blotted onto nylon membranes and randomly primed $^{32}$P-labelled probe of either NPT II gene or 5'-470 bp OMT CDNA fragments was synthesized using a DECA II DNA labelling kit. Hybridization was conducted according to Church and Gilbert, Proc. Natl. Acad. Sci. USA 86:1991–1995 (1984) with the exception that 0.25M sodium phosphate buffer (pH 7.4) as used. The blot was washed twice at 65° C. with 2 X SSC/0.5% SDS, twice with 0.1 X SSC/0.1% SDS and autoradiographed on X-ray film at −80° C. using an intensifying screens. The same blot was stripped in 0.2N NaOH and 0.1% SDS at 37° C. for 30 minutes, prehybridized, and then reprobed with different $^{32}$P-labelled gene probes.

Southern hybridization demonstrated the integration of the antisense OMT gene construct in the nuclear genome of transgenic plants analyzed but not in that of non-transformed control. Hybridization signals were seen for the transgenic plants when $^{32}$P-labeled NPT II DNA was used as a probe. The integration of antisense OMT gene in transgenic plants was further confirmed when the blots were reprobed with $^{32}$P-labeled OMT DNA fragment. The hybridizing patterns of endogenous OMT gene, as seen in non-transformed control plants, were disturbed in almost all the transgenic plants. This was obviously due to the integration of the antisense OMT gene cassette into the genome of the transgenic plants.

Multiple integration patterns of antisense OMT gene in various transgenic plants originated from the same leaf disc were also observed. Because the transgenic plants were regenerated from callus via organogenesis, it is possible that many transformation events might be co-induced nearby in one leaf disc and failed to be separated in subsequent subcultures. These results indicate that there is a need to perform Southern hybridization for every individual transgenic plants obtained via organogenesis in order to correctly define the cell line according to the hybridization profile. To obtain multiple transgenic cell lines from a single leaf disc through callus induction and organogenesis is actually advantageous since it increases the number of independent transgenic plants and thus increases the probability to score the most desirable transgenic plants.

When the genomic DNA of the transgenic plants were double digested with Hind III and Xba I and probed with labeled 35S promoter fragment, a hybridizing DNA fragment was found at about 0.7 kb, which is the expected size for the 35S enhancer-promoter/AMV RNA4 fragment. The lanes for plasmid DNA of pAOMT2 (control) and genomic DNA from GUS plant also revealed a strong hybridizing DNA fragment at the same size.

This is expected since the GUS gene integrated into nuclear genome of the GUS plant was also driven by the 35S enhancer-promoter/AMV RNA4 as described above.

Based on the intensity of hybridizing bands in this blot, some transgenic plants apparently had higher copy numbers of the antisense OMT gene than others.

The expression of antisense OMT gene in transgenic plants was further examined by Northern analysis. Total RNA from young leaves of transgenic plants was isolated according to Bugos et al. BioTechniques 19(5):734–737 (1995). Two grams of leaf tissue was frozen in liquid nitrogen and ground to a fine powder using a prechilled mortar and pestle. The powdered frozen tissue was transferred into a polypropylene centrifuge tube and homogenized in 10 mL of RNA extraction buffer (100 mM Tris HCl pH 9.0, 200 mM NaCl, 15 mM EDTA, 0.5% sarkosyl, and 100 mM 2-mercaptoethanol), 10 mL of equilibrated phenol and 2 mL of chloroform isoamyl alcohol (24:1) using a homogenizer at high speed for 3 minutes. 0.7 mL of 3M sodium acetate (pH 5.0) was then added and homogenized for another 30 seconds. The homogenate was incubated on ice for 30 minutes and centrifuged at 16,000 xg for 10 minutes at 4° C. The aqueous phase was precipitated with an equal volume of isopropanol, chilled at −80° C. for 30 minutes and pelleted the RNA by centrifugation at 10,000 xg for 10 minutes at 4° C. The pellet was washed with 70% ethanol, dried in a vacuum and resuspended in 500 $\mu$L of DEPC-treated water. Since the RNA samples so obtained were very viscous indicating the co-presence of secondary metabolites, the RNA samples were subjected to further extraction. To the RNA were added an equal volume of 2 X RNA extraction buffer, 2 vol of phenol, 0.4 vol of chloroform: isoamyl alcohol (24:1) and 0.14 vol of sodium acetate (pH 5.0), mixed, and centrifuged at 14,000 rpm for 10 minutes at 4° C. The aqueous phase was extracted one more time with phenol and chloroform:isoamyl alcohol and precipitated with an equal volume of isopropanol. The RNA pellet was dissolved in 880 $\mu$L of DEPC-treated water and reprecipitated at 4° C. overnight by addition of 400 $\mu$L of 8M LiCl (2.5M final concentration). RNA was recovered by centrifugation and resuspended in 500 $\mu$L of DEPC-treated water. Twenty $\mu$g of total RNA was fractionated on a denaturing gel containing 1% agarose and 2.2M formaldehyde following denaturation of samples in formaldehyde and formamide in the presence of ethidium bromide to allow visualization of RNA after electrophoresis. RNA was transferred to a nylon membrane by capillary transfer in 20 X SSC overnight and immobilized in a UV-crosslinker.

Since the analyzed transgenic plants all contain the homologous OMT antisense gene construct based on the Southern analyses, a dig-labeled sense ssDNA probe was synthesized through PCR and used in Northern hybridization to detect only the antisense transcripts derived from the introduced antisense OMT gene. The 5'-470 bp bi-OMT DNA fragment was used as a template and the upstream primer used in closing PTOMT was employed to generate the sense ssDNA probe. The reaction contained 10 mM KCl, 20 mM Tris-HCl (pH 8.8), 10 mM $(NH_4)_2SO_4$, 3 mM $MgSO_4$ 0.1% Triton, 40 $\mu$M each of dATP, dCTP, and dGTP, 36 $\mu$M dTTP, 4 $\mu$M digoxigenin-11-dUTP, 0.1 $\mu$M primer, 50 ng of template DNA, and 4 units of Deep Vent (exo$^-$) DNA polymerase in a final volume of 100 $\mu$L. The reaction was performed in a thermal cycler using the following conditions: 55 cycles of 95° C./45 sec, 55° C./30 sec, and 72° C./45 sec, and final extension 72° C./5 min. The PCR products were used in Northern hybridization without further purification. Prehybridization, hybridization and chemiluminescence detection of RNA blot was carried out according to the manufacturer's instructions.

Of the transgenic plants analyzed, approximately one half showed hybridization at about 0.7 kb, the size expected for the antisense bi-OMT mRNA. No hybridizing signal was detected on the other transgenic plants and non-transformed control plant. The absence of antisense transcripts in the Northern blot has also been reported in other studies. It was noted in these cases that antisense RNA can have a significant effect even if little or none is detectable by Northern analysis. This is probably because of the formation of antisense RNA-mRNA duplex, one of the proposed mechanisms of antisense inhibition, which results in a rapid degradation of the antisense RNA. Because the antisense RNA inhibition is believed to occur primarily in the nucleus, it is also pointed out that hybridizing to total RNA, which usually contains a majority of cytoplasmic RNA by common extraction method, is a poor indicator of the level of antisense transcripts in the nucleus. Cytoplasmic levels might probably indicate only those RNA that has escaped from degradation in the nucleus.

The OMT enzyme activity assay was also conducted according to Bugos et al., Phytochem 31(5):1495–1498 (1992). Crude protein was extracted from developing xylem tissue of transgenic plants harvested in the growth season using extraction buffer containing 0.5M Tris-HCl (pH 7.4), 1 mM EDTA, 40 mM ascorbic acid, 30% (w/v) glycerol, 2.5% (w/v) PVPP, 1 mM PMSF, 0.1 $\mu$M Leupeptin, and 5 mM mercaptoethanol. The OMT activity assays were performed in triplicate. The reaction mixture (200 $\mu$L) contains 50 mM Tris-HCl (pH 8), 10 mM $MgCl_2$, 1 mM phenylpropanoid substrate (caffeic or 5-hydroxyferulic acid) and 50 $\mu$L crude enzyme solution in a 1.5 mL microcentrifuge tube. After preincubate for 5 minutes at 30° C., 100 nmol of diluted SAM-$^{14}$ME (1 μL) is added and the reaction is incubated for 10 minutes at 30° C. The reaction is terminated by the addition of 20 μL of 2M HCl. Diethyl ether (1 mL) is added and the content is vortexed vigorously and centrifuged briefly to separate the aqueous and organic phases. The reaction mixture is placed at −70° C. for 30 minutes to freeze the aqueous phase and the ether is transferred to a scintillation vial. Radioactivity is determined by liquid scintillation after addition of 5 mL Bio-Safe II counting cocktail.

The results of OMT enzyme activity of control and transgenic aspens correlate well with the results of Southern and Northern hybridization in which specific transgenic plants also shows a high T-DNA copy numbers (Southern) and a high level of antisense message (Northern).

The lignin content of control and transgenic aspens is determined by both klason (TAPPI Official Test Method T222) and acetyl bromide method of Iiyama and Wallis, Wood Sci. Technol. 23;271–280 (1988). No statistically significant difference is observed in the lignin content of control and transgenic aspens.

Lignin structure is also analyzed by nuclear exchange reaction according to Funaoka et al., Methods in Lignin Chemistry, pp. 369–384 (1992). Guaiacyl and syringyl contents in woody tissue is determined through quantitative conversion of guaiacyl and syringyl units in lignin into guaiacol and pyrogallol derivatives, respectively, in a reaction medium consists of boron trifluoride ($BF_3$) and excess phenol. The quantities of these reaction products, representing the quantities of guaiacyl and syringyl units, is determined by GC/MS.

The lignin structure of the transgenic aspens harboring the antisense OMT gene construct was altered. For example, in one particular transgenic line analyzed, the guaiacyl lignin content was significantly increased by 49.5% and the syringyl lignin content was reduced by 40.6%. This increased guaiacyl lignin content (G) and decreased syringyl lignin content (S) led to a 60% reduction in the syringyl to guaiacyl lignin (S/G) ratio when compared to that of the control aspen.

It is well known that the rate of kraft delignification is directly proportional to the S/G ratio in wood. Partial kraft delignification was therefore conducted for control and several transgenic aspen lines in order to confirm the correlation between the lignin structure and pulping efficiency. The dramatic decrease in S/G ratio of the transgenic aspen significantly impaired the pulping efficiency, causing a lignin removal in one example of less than 12% as compared to a 54% removal of lignin from control aspen. This is well as expected since the incorporation of antisense OMT construct into transgenic aspens suppresses the expression of endogenous OMT gene and therefore reduces the formation of syringyl lignin.

EXAMPLE IV

Using the above described transformation and regeneration method, an aspen O-methyltransferase gene driven by cauliflower mosaic virus (CaMV) 35S promoter (pFOMT1 as shown in FIG. 2) was introduced into sweetgum (*Liquidambar styraciflua*). The lignin composition was analyzed using the methods described above. The lignin composition had been altered such that the ratio of syringyl to guaiacyl units had increased.

EXAMPLE V

Using the above described transformation and regeneration method, aspen O-methyltransferase gene driven by cauliflower mosaic virus (CaMV) 35S promoter (pFOMT1 as shown in FIG. 2) was introduced into quaking aspen. The lignin composition was analyzed using the methods described above. The ratio of syringyl to guaiacyl units had decreased. When introducing the homologous OMT gene back into aspen in a sense orientation, the homologous gene acted like it was in the antisense orientation in that the guaiacyl lignin content was increased and the syringyl lignin content was reduced and accordingly the ratio of syringyl to guaiacyl units decreased.

We claim:

1. A method for transforming and regenerating greenhouse-grown or field-grown Populus species comprising:

mobilizing a gene construct including a lignin pathway gene into a species of Agrobacterium;

excising a leaf piece from the greenhouse-grown or field-grown Populus species;

inoculating the leaf piece with the Agrobacterium species and the phenolic compound acetosyringone for less than thirty minutes without first preculturing the leaf piece;

co-cultivating the leaf piece on woody plant medium in the dark;

washing the leaf piece to kill the Agrobacterium;

transferring the leaf piece to woody plant media containing an antibiotic, BA and 2,4-D;

excising formed calli;

transferring the formed calli to woody plant media containing an antibiotic and thidiazuron;

separating formed shoots; and placing the shoots in media for rooting of the transgenic plant.

2. A method for transforming and regenerating greenhouse-grown or field-grown Populus species as set forth in claim 1 wherein the species of Agrobacterium is tumefaciens.

3. A method for transforming and regenerating greenhouse-grown or field-grown Populus species as set forth in claim 1 and further including the step of sterilizing the excised leaf piece.

4. A method for transforming and regenerating greenhouse-grown or field-grown Populus species as set forth in claim 1 wherein the antibiotic is kanamycin.

5. A method for transforming and regenerating greenhouse-grown or field-grown Populus species as set forth in claim 1 wherein the lignin pathway gene is O-methyltransferase.

6. A method for transforming and regenerating greenhouse-grown or field-grown Populus species as set forth in claim 1 wherein the leaf piece is co-cultivated in the dark for about two days.

7. A method for transforming and regenerating greenhouse-grown or field-grown Populus species as set forth in claim 1 and further including transplanting the transgenic plant into soil.

8. A method for transforming and regenerating greenhouse-grown or field-grown Populus species as set forth in claim 1 wherein the species of Agrobacterium lacks a plasmid containing phytohormone genes.

9. A method for transforming and regenerating greenhouse-grown or field-grown Populus species comprising:

mobilizing a gene construct including a lignin pathway gene into a species of Agrobacterium;

excising a leaf piece from the greenhouse-grown or field-grown Populus species;

inoculating the leaf piece with the Agrobacterium species and a phenolic compound for less than thirty minutes without first preculturing the leaf piece;

co-cultivating the leaf piece on woody plant medium;

transferring the leaf piece to woody plant media containing an antibiotic;

excising formed calli;

transferring the formed calli to woody plant media containing an antibiotic and thidiazuron;

separating formed shoots; and placing the shoots in media for rooting of the transgenic plant.

10. A method for transforming and regenerating greenhouse-grown or field-grown Populus species as set forth in claim 9 wherein the phenolic compound is acetosyringone.

11. A method for transforming and regenerating greenhouse-grown or field-grown Populus species as set forth in claim 9 wherein in the step of transferring the leaf piece to woody plant media containing an antibiotic, the woody plant media contains BA and 2,4-D.

12. A method for transforming and regenerating greenhouse-grown or field-grown Populus species as set forth in claim 9 wherein the species of Agrobacterium is tumefaciens.

13. A method for transforming and regenerating greenhouse-grown or field-grown Populus species as set forth in claim 9 wherein the antibiotic is kanamycin.

14. A method for transforming and regenerating greenhouse-grown or field-grown Populus species as set forth in claim 9 wherein the lignin pathway gene is O-methyltransferase.

15. A method for transforming and regenerating greenhouse-grown or field-grown Populus species as set forth in claim 9 wherein the leaf piece is co-cultivated in the dark for about two days.

16. A method for transforming and regenerating greenhouse-grown or field-grown Populus species as set forth in claim 9 and further including transplanting the transgenic plant into soil.

17. A method for transforming and regenerating greenhouse-grown or field-grown Populus species as set forth in claim 9 wherein the species of Agrobacterium lacks a plasmid containing phytohormone genes.

18. A method for transforming and regenerating greenhouse-grown or field-grown Populus species as set forth in claim 9 and further including washing the leaf piece to kill the Agrobacterium using claforan and ticarcillin.

19. A method for transforming and regenerating Populus species comprising:

mobilizing a gene construct including a lignin pathway gene into a species of Agrobacterium;

excising a leaf piece from the Populus species;

inoculating the leaf piece with the Agrobacterium species and a phenolic compound;

placing the inoculated leaf piece on woody plant media containing an antibiotic;

excising formed calli;

transferring the calli to woody plant media containing an antibiotic and thidiazuron;

separating formed shoots; and placing the shoots in media for rooting of the transgenic plant.

20. A method for transforming and regenerating Populus species as set forth in claim 19 wherein the species of Agrobacterium is tumefaciens.

21. A method for transforming and regenerating Populus species as set forth in claim 19 wherein the excised leaf piece is excised along the midrib.

22. A method for transforming and regenerating Populus species as set forth in claim 19 wherein the phenolic compound is acetosyringone.

23. A method for transforming and regenerating Populus species as set forth in claim 19 and further including the step of sterilizing the excised leaf piece.

24. A method for transforming and regenerating Populus species as set forth in claim 19 wherein the leaf piece is inoculated with the Agrobacterium species and a phenolic compound for less than thirty minutes.

25. A method for transforming and regenerating Populus species as set forth in claim 19 wherein the step of excising a leaf piece from the Populus species includes excising a leaf piece from a greenhouse-grown or field-grown species.

26. A method for transforming and regenerating Populus species as set forth in claim 19 wherein the antibiotic is kanamycin.

27. A method for transforming and regenerating Populus species as set forth in claim 19 wherein the lignin pathway gene is O-methyltransferase.

28. A method for transforming and regenerating Populus species as set forth in claim 19 wherein the step of placing the inoculated leaf piece on woody plant media containing an antibiotic includes co-cultivating the leaf piece in the dark.

29. A method for transforming and regenerating Populus species as set forth in claim 19 wherein after co-cultivation, the leaf piece is washed to kill the Agrobacterium.

30. A method for transforming and regenerating Populus species as set forth in claim 19 and further including transplanting the transgenic plant into soil.

31. A method for transforming and regenerating Populus species as set forth in claim 19 wherein the species of Agrobacterium lacks a plasmid containing phytohormone genes.

32. A method for transforming and regenerating Populus species as set forth in claim 19 wherein the step of placing the inoculated leaf piece on woody plant media containing an antibiotic includes the use of woody plant media containing BA and 2,4-D.

33. A method for transforming and regenerating Populus species as set forth in claim 19 wherein the step of inoculating the leaf piece with the Agrobacterium species and a phenolic compound includes inoculating the leaf piece after excision without first preculturing the leaf piece.

* * * * *